(12) United States Patent
Clasen et al.

(10) Patent No.: US 11,369,461 B2
(45) Date of Patent: Jun. 28, 2022

(54) DISPOSABLE ASPIRATOR

(71) Applicant: Cleverdent Ltd., Münster (DE)

(72) Inventors: Stephan Clasen, Münster (DE); Martin Kayser, Cologne (DE)

(73) Assignee: Cleverdent Ltd., Münster (DE)

( * ) Notice: Subject to any disclaimer, the term of this patent is extended or adjusted under 35 U.S.C. 154(b) by 85 days.

(21) Appl. No.: 16/337,430

(22) PCT Filed: Sep. 26, 2017

(86) PCT No.: PCT/EP2017/074357
§ 371 (c)(1),
(2) Date: Mar. 28, 2019

(87) PCT Pub. No.: WO2018/060188
PCT Pub. Date: Apr. 5, 2018

(65) Prior Publication Data
US 2020/0038156 A1    Feb. 6, 2020

(30) Foreign Application Priority Data

Sep. 28, 2016    (DE) ..................... 10 2016 011 629.3

(51) Int. Cl.
*A61C 17/08*    (2006.01)
*A61B 1/00*    (2006.01)
(Continued)

(52) U.S. Cl.
CPC .......... *A61C 17/08* (2019.05); *A61B 1/00103* (2013.01); *A61B 1/253* (2013.01); *A61B 1/015* (2013.01)

(58) Field of Classification Search
CPC ..... A61C 17/08; A61C 17/088; A61C 17/084; A61B 1/247; A61B 1/00103; A61B 1/253; A61B 1/015
See application file for complete search history.

(56) References Cited

U.S. PATENT DOCUMENTS 1,764,455 A * 6/1930 Kulik .................. A61B 1/247
433/31
2,428,975 A * 10/1947 Lamb .................. A61B 1/07
362/573
(Continued)

FOREIGN PATENT DOCUMENTS

CH          543880        11/1973
DE       102012100119     12/2012
(Continued)

OTHER PUBLICATIONS

Mitteilung Gemaess Artikel 94 (3) EPU [Comunication Pursuant to Article 94(3) EPC] dated Mar. 11, 2020 From the European Patent Office Re. Application No. 17784870.2. (5 Pages).
(Continued)

*Primary Examiner* — Nicholas D Lucchesi

(57) ABSTRACT

The invention relates to a dental mirror suction device (10) for suctioning liquids and particles from an oral cavity of a patient, with a tubular hollow base body (12) having an inner surface (14), an outer surface (16), a longitudinal axis (X-X), a connection opening (18) for a hose, and a suction opening (20). The inner surface (14) has a mirror-coated surface (24) which is viewable through the suction opening (20) and which is arranged such that the oral cavity is viewable at least in some portions. The mirror suction device (10) is configured as a disposable mirror suction device.

4 Claims, 2 Drawing Sheets

(51) Int. Cl.
*A61B 1/253* (2006.01)
*A61B 1/015* (2006.01)

(56) References Cited

U.S. PATENT DOCUMENTS

| | | | | |
|---|---|---|---|---|
| 3,928,916 | A * | 12/1975 | Hansson | A61B 1/247 433/31 |
| 4,568,281 | A * | 2/1986 | Harvey | A61B 1/253 219/219 |
| 4,925,391 | A * | 5/1990 | Berlin | A61B 1/253 433/31 |
| 6,932,601 | B2 * | 8/2005 | Frider | A61C 17/08 433/31 |
| 7,553,158 | B2 * | 6/2009 | Frider | A61B 1/00094 433/31 |
| 8,282,393 | B2 * | 10/2012 | Widen | A61C 17/0202 433/31 |
| 8,608,472 | B2 * | 12/2013 | Clasen | A61C 17/08 433/91 |
| 10,786,139 | B2 * | 9/2020 | Clasen | A61C 17/088 |
| 2003/0076605 | A1 * | 4/2003 | Shohet | A61B 1/247 359/840 |
| 2005/0106527 | A1 * | 5/2005 | Frider | A61C 17/08 433/31 |
| 2007/0148611 | A1 * | 6/2007 | Frider | A61C 17/08 433/31 |
| 2009/0311648 | A1 * | 12/2009 | Clasen | A61B 1/247 433/31 |
| 2016/0227987 | A1 * | 8/2016 | Clasen | A61B 1/247 |
| 2019/0298163 | A1 * | 10/2019 | Tavor | A61B 1/253 |
| 2019/0336255 | A1 * | 11/2019 | Clasen | A61B 1/253 |
| 2019/0343378 | A1 * | 11/2019 | Clasen | A61B 1/247 |
| 2020/0030068 | A1 * | 1/2020 | Clasen | A61C 17/12 |

FOREIGN PATENT DOCUMENTS

| | | |
|---|---|---|
| DE | 102013110302 | 3/2015 |
| FR | 2595939 | 9/1987 |

OTHER PUBLICATIONS

Internationaler Recherchenbericht und der Schriftliche Bescheid [International Search Report and the Written Opinion] dated Jan. 5, 2018 From the International Searching Authority Re. Application No. PCT/EP2017/074357 and Its Translation of Search Report Into English. (13 Pages).

* cited by examiner

DISPOSABLE ASPIRATOR

RELATED APPLICATIONS

This application is a National Phase of PCT Patent Application No. PCT/EP2017/074357 having International filing date of Sep. 26, 2017, which claims the benefit of priority of German Patent Application No. 629.3 011 2016 10 filed on Sep. 28, 2016. The contents of the above applications are all incorporated by reference as if fully set forth herein in their entirety.

FIELD AND BACKGROUND OF THE INVENTION

The present invention relates to a dental mirror suction device for suctioning liquids and particles from an oral cavity of a patient, with a hollow base body having an outer surface, an inner surface, a longitudinal axis, a connection opening, and a suction opening.

Dental treatments often require that emerging liquids or dissolved particles, such as saliva, spray water and blood, be suctioned off during treatment. Also, water, for example for cleaning or after using a multi-function syringe, may accrue, which has to be suctioned off. Usually, mirror suction devices are used for this purpose, which are generally formed from a tubular body of plastic, to whose end a hose is attached, which in turn is connected to a pump. The distracting liquids and solids are carried away through the hose.

A mirror suction device is often not guided and held by the attending dentist or dental surgeon himself but by an assistant, because the attending dentist has to hold a drilling tool with the one hand and a mirror with the other, with which he is able to inspect the area to be treated. The above-described procedure is disadvantageous in that the two people have to stand or sit very close to each other, around the area to be treated. Particularly if the interventions are rather difficult or demanding with regard to fine-motor skills, this may be perceived as distracting by the attending physician.

A medical mirror suction device in which the inner surface has a mirror-coated surface which is visible through the suction opening is known from DE 102006048463 A1. The reflective coating according to the invention enables the user to use the medical mirror suction device both as a mirror suction device for removing liquids and particles and, simultaneously, as a mirror. Using such a mirror suction device, it is now possible for him to carry out the treatment without an assisting person.

Thus, the mirror suction device is simultaneously used as a mirror suction device and as a mirror. The basic concept of the combination is very good in principle, however, production is complex and involves high costs. In addition, the effort for cleaning and sterilizing the mirror suction devices is also great.

SUMMARY OF THE INVENTION

The object of the present invention is to provide a mirror suction device which is improved over the known mirror suction device. The former is supposed also to offer the possibility of inspecting the oral cavity during suctioning. In particular, the mirror suction device is supposed to be cost-effective to produce.

According to the invention, the object is achieved with a mirror suction device having the features of claim 1.

Accordingly, the mirror suction device is configured as a disposable mirror suction device. Thus, the otherwise customary cleaning and sterilization after the treatment can be omitted; a new mirror suction device is used for each patient.

In order to reduce the costs connected to the one-off use, the mirror suction device according to the invention is made from inexpensive components. In particular, an otherwise customary glass mirror is not used. A metal disk, preferably consisting of highly polished steel with a high-quality surface finish, a film or a reflective surface which is, for example, vapor-coated with chromium, may be used instead of the glass mirror. A paint coating is also conceivable. What is essential is that the mirror or the reflective surface used can be produced at lower costs than a customary glass mirror.

In a particularly advantageous variant of the embodiment, the mirror suction device has a base body consisting of only a single part. The base body is made from only a single material and can preferably be produced in only a single production step. In the region of the suction opening, the base body forms a surface which is as planar as possible and is provided with a reflective material. The reflective material may be, for example, a film glued to the planar surface. Alternatively, it is possible to mirror-coat the planar surface, preferably to vapor-coat it with chromium, or to paint it with a reflective paint. Thus, production in a quick and simple manner is possible; the costs are low.

According to the invention, the mirror suction device may also be formed from two base body parts, which are connected to each other, preferably welded or glued to each other, and thus ultimately form a quasi-integral mirror suction device. Within the sense of the invention, quasi-integral means that after production, the two base body parts can be separated from each other only destructively. If the base body consists of two base body parts, an inexpensive mirror member is also used.

The mirror member according to the invention is preferably formed from either a reflective metal disk or a plastic disk provided with a reflective film or another coating applied thereto. In particular, the coating can be produced by vapor-coating, preferably with chromium.

In a particularly advantageous variant of an embodiment, the plastic disk consists of the same plastic as the rest of the base body or the rest of the base body parts. This is advantageous in that only a single material has to be procured for manufacture. Furthermore, this is advantageous for production, because production can be carried out under constant physical conditions, e.g. with respect to temperature and pressure.

For example, the base body of the mirror suction device may also be formed from two longitudinal halves retaining the mirror member in a groove. The mirror member, as it were, is thus disposed between the two longitudinal halves and surrounded in some portions of its outer circumference by the two longitudinal halves.

In a particularly advantageous variant of an embodiment, the mirror suction device according to the invention is formed from two base body parts, wherein the mirror member is retained in a mirror-accommodating portion of the first base body part in an opening whose inner wall forms an upper retaining shoulder abutting against an outer wall of the mirror member, wherein the upper retaining shoulder is formed by the first base body part and surrounds the entire outer circumference of the mirror member, the opening of the first base body part tapers from an underside of the base body in the direction towards the suction opening and has a diameter, on its side facing towards the underside of the base body, which is greater than the diameter of the mirror member, the two base body parts are connected to each other in a gap-free manner in such a way that, together, they integrally form the base body.

An essential insight is that an attractive outer appearance of the base body is obtained when one of the two first base body parts is as large as possible and the other base body part is as small as possible and the smaller base body part extends in the longitudinal direction of the mirror suction device only to a small extent. Thus, the distracting groove or distracting burr produced by the connecting surfaces between the base body parts is relatively short.

Furthermore, it is crucial that the smaller base body part and the connection between the base body parts are disposed in a region that the attending physician does not touch at all, or only to a little extent, during the treatment. Even if the connecting surfaces have a negative effect on the surface of the mirror suction device, they do not result in a haptic distraction.

The arrangement in the region of the back of the mirror, i.e. at the underside of the mirror suction device, is particularly advantageous because the region is generally not visible during the use of the mirror suction device. Thus, variations in the surface, which cannot be felt by touch but are visible, hardly stand out in a negative way.

Thus, the first base body part forms almost the entire base body of the mirror suction device, whereas the second base body part substantially only seals the opening required for inserting the mirror into the first base body part. Relative to the outer surface, the first base body part has a percentage of the surface of 80 to 95%, and the second base body part has a percentage of the surface of 5 to 20%.

Advantageously, the mirror member is circular, but may also be oval or have other suitable shapes. The following is based on the customary circular shape of the mirror member.

In order to permanently hold the mirror member in a reliable manner, the first base body part has a mirror-accommodating portion with an opening for inserting the mirror member. Thus, the first base body part laterally surrounds the mirror inserted into the opening. In the finished mirror suction device, the opening is sealed at the back, i.e. behind the inserted mirror, by the second base body part. The two base body parts are welded or glued to each other.

The visible surface of the mirror member remains clear and is visible from the front. In an advantageous variant of an embodiment, the second base body part disposed on the back of the mirror member, as a whole, has dimensions that exceed the dimensions of the mirror member only to an insubstantial extent. It is thus possible to first produce the first base body part, then insert the mirror member from the back into the free opening in the first base body part and finally seal the opening from the back with the second base body part.

According to the invention, the opening in the first base body part tapers in the direction towards a bottom surface within the base body in the region of the suction opening; it is configured and dimensioned such that the inserted mirror, in the mirror-accommodating portion, abuts against an upper retaining shoulder formed in an inner wall of the opening.

What is essential is that the opening of the mirror-accommodating portion of the first base body part is dimensioned such that the mirror member can be inserted into the mirror-accommodating portion. Therefore, the opening, on the side thereof facing towards the rear of the base body, has a diameter exceeding the diameter of the mirror member. Accordingly, the second base body part also has a diameter exceeding the diameter of the mirror member. In the vertical cross-sectional direction, the opening is ultimately a conically tapering passage into which the mirror member is inserted from the wider side. These explanations refer to a circular basic shape of the mirror member; if the latter has a different shape, the mirror-accommodating portion has to be configured in such a manner that this other shape can also be accommodated.

In a particularly advantageous variant of an embodiment, the mirror member, in the vertical cross section, is configured to be substantially trapezoidal, wherein the diameter of the mirror member grows starting from a mirror surface in the direction towards the underside of the base body. As was already explained, the inner wall of the opening of the first base body part has a vertical cross section corresponding thereto; its diameter grows starting from the underside of the base body.

Advantageously, the trapezoidal shape of the outer wall of the mirror member and of the inner wall of the opening or the upper retaining shoulder are selected such that the visible mirror surface, in the inserted state of the mirror member, ends flush with the bottom surface of the first base bottom part surrounding the mirror surface. By abutting against the outer side of the mirror surface, the upper retaining shoulder prevents the mirror member from being able to protrude upwards over the bottom surface or become detached from the base body in that direction.

Advantageously, the mirror member is retained in a frictional or positive manner already when it is inserted into the mirror member accommodating portion. For example, the diameter of the opening can be configured to be minimally smaller than the diameter of the mirror member. In that case, the mirror member, when inserted, deforms the surrounding material, and pushes it back slightly, so that the mirror member is subsequently retained by the elastic material. Then, the second base body part is glued or molded onto the first base body part with the mirror inserted and retained therein.

Alternatively, it is also conceivable that not the entire diameter of the opening is smaller than the diameter of the mirror member, but that only several, preferably three, raised portions evenly distributed over the course of the inner wall or retaining shoulder are provided, which retain the mirror member in its position already prior to the connection with the second base body part.

The mirror surface and the surrounding bottom surface form as planar an overall surface as possible, via which the air flow, suctioned-off liquid and particles can be carried away in an optimal manner. The planar overall surface also causes the noise development due to air turbulence in this region to be low. A protrusion of the mirror member over the bottom surface of the first base body part of up to 0.3 mm is still considered to be flush in the sense of the invention.

As an alternative to the plain trapezoidal shape, the mirror member may have a maximum diameter, for example in the central area of its vertical cross section. Thus, the diameter first increases, starting from the mirror member surface, and then decreases again in the direction towards the back of the mirror member. The inner wall of the opening is then configured correspondingly, so that the mirror member can be snapped into the mirror-retaining groove thus formed. In that case, the inner wall of the opening not only forms an upper retaining shoulder, but also a lower retaining shoulder. It is also conceivable that the lower retaining shoulder, which the mirror member, starting from the back thereof, contacts even before its maximum diameter, is formed by the second base body part.

The second base body part can be connected to the first base body part and have a corresponding shape, in such a manner that it pushes the mirror member within the opening against the upper retaining shoulder under a bias. This ensures that the mirror member is retained securely and is unable to move even during the treatment. The inner wall of the opening serves as a sealing lip and, similar to a shaft seal ring, abuts the mirror side surface peripherally.

A thermoplastic synthetic material, such as polypropylene or also polyethylene, is particularly suitable for production. By adding additives, the outward appearance of the mirror suction device may be influenced.

The mirror member is not located in front of the suction opening, but substantially behind the suction opening in the flowing direction of the suctioned air, i.e. within the base body. It is thus achieved that the mirror suction device is not made longer by an upstream mirror, which would reduce the suctioning performance.

Even though gluing the base body part together is possible in principle, it has proved to be particularly advantageous to weld the two base body parts together and not use any adhesive. The disadvantages, which adhesives generally involve, may thus be avoided.

Advantageously the first base body part can be produced and configured such that the mirror member is frictionally or positively retained in the first base body part already prior to the connection of the two base body parts. This simplifies the following production steps.

BRIEF DESCRIPTION OF THE SEVERAL VIEWS OF THE DRAWINGS

The invention is explained further with reference to the following figures. They merely show exemplary embodiments; the invention is not supposed to be limited thereto.

In the Figures.

DESCRIPTION OF SPECIFIC EMBODIMENTS OF THE INVENTION

Figure 1:
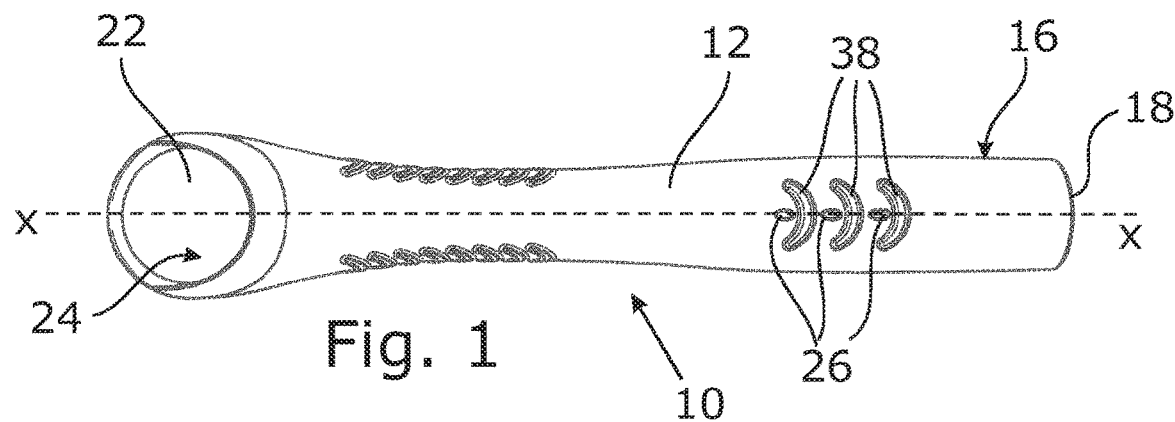
FIG. 1: shows a mirror suction device according to the invention from above.
Figure 2:
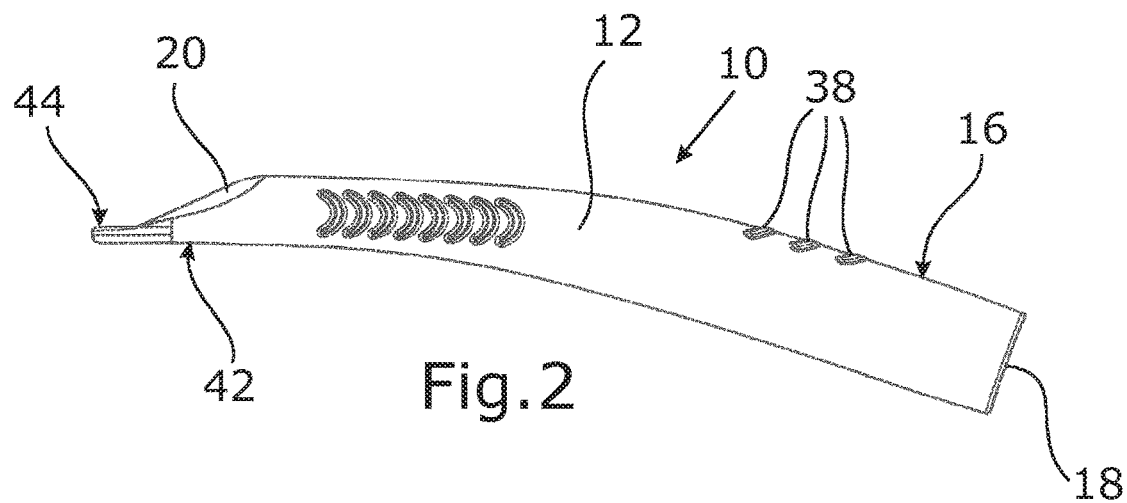
FIG. 2: shows the mirror suction device according to the invention of FIG. 1 from the side.
Figure 3:
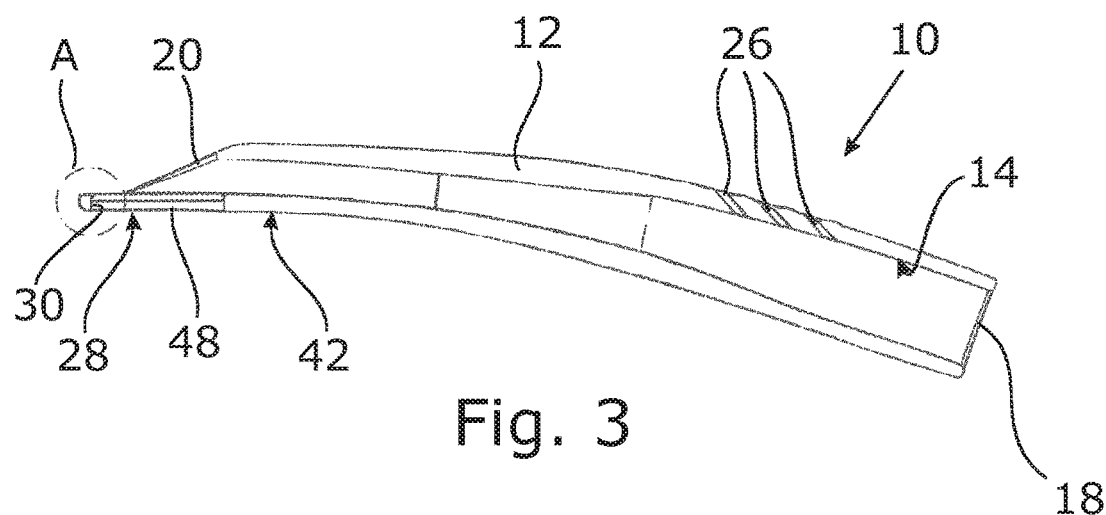
FIG. 3: shows the mirror suction device according to the invention of FIG. 1 in a longitudinal section.

As is apparent, in particular, from FIGS. 1 to 3, a mirror suction device 10 according to the invention has a hollow, tubular base body 12 with an inner surface 14 and an outer surface 16. Moreover, the base body 12 has a longitudinal axis X-X (see FIG. 1). The arc shape of the mirror suction device 10, which is recognizable particularly in FIGS. 2 and 3, is advantageous in that it is easier to guide towards the site to be treated.

The base body 12 has a connection opening 18 for a hose, which is not shown, and a suction opening 20 for suctioning particles and liquids. The liquids or particles to be suctioned off are sucked through the connection opening 20 and carried away through the connection opening 18 via the hose.

According to the invention, a mirror member 22, which is viewable through the suction opening 20, is disposed within the base body 12 in the region of the suction opening 20. Accordingly, the visible mirror surface 24 faces towards the suction opening 20. The mirror member 22 is disposed in its entirety within the base body 12, i.e. behind the suction opening 20 as viewed in the flowing direction of the air to be suctioned off. The suctioned air is guided over the mirror surface 24, whereby fogging of the mirror member surface 24 is effectively prevented.

The mirror member 22 according to the invention is preferably formed from either a reflective metal disk or a plastic disk provided with a reflective film or another coating applied thereto. In particular, the coating can be produced by evaporation, preferably with chromium.

The mirror suction device 10 may have additional openings 26 through which air is also suctioned. The additional openings 26 prevent a negative pressure within the base body 12 if the suction opening 20 is sealed by the tongue or cheek of the patient, for example. Three additional openings 26 are provided in the exemplary embodiment, however, only a single additional opening 26 or even more than three additional openings 26 are also conceivable.

Profile members 38, which provide for a safe grip of the mirror suction device 10 and prevent the fingers of the attending dentist from slipping, are discernible on the outer surface 16 of the base body 12.

Figure 6:
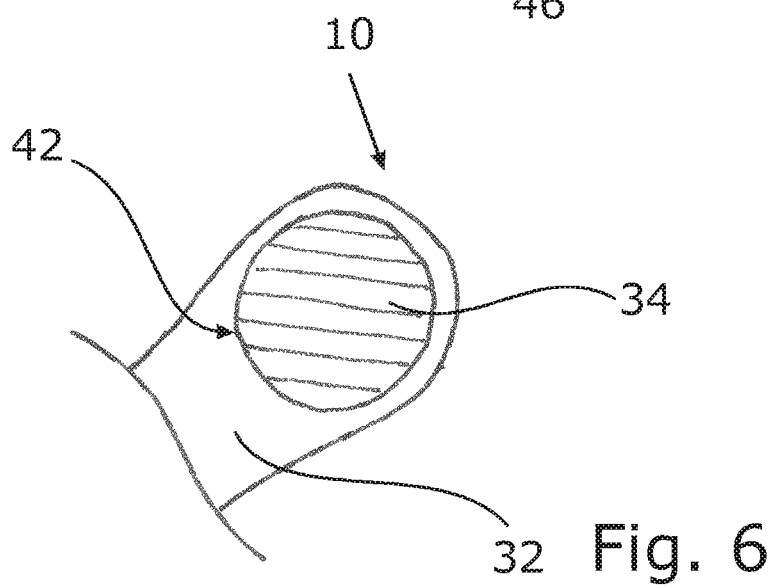
FIG. 6: shows a simplified illustration of the front region of the mirror suction device from below.

FIGS. 3 and 6 show that the base body 12 is formed from a first base body part 32 and a second basic body part 34. The first base body part 32 has a mirror-accommodating portion 48 with an opening 28, in which the mirror member 22 is inserted in the assembled state. An inner wall 30 of the opening 28 surrounds the mirror member 22 and abuts against an outer wall 36 of the mirror member 22 at least in some portions. The opening 28 tapers starting from an underside 42 of the base body in the direction towards the suction opening 20. The opening 28, on the side thereof facing towards the underside 42 of the base body, has a diameter greater than the diameter of the mirror member 22. This is required for the mirror member 22 to be insertable into the mirror-accommodating portion 48.

Figure 5:
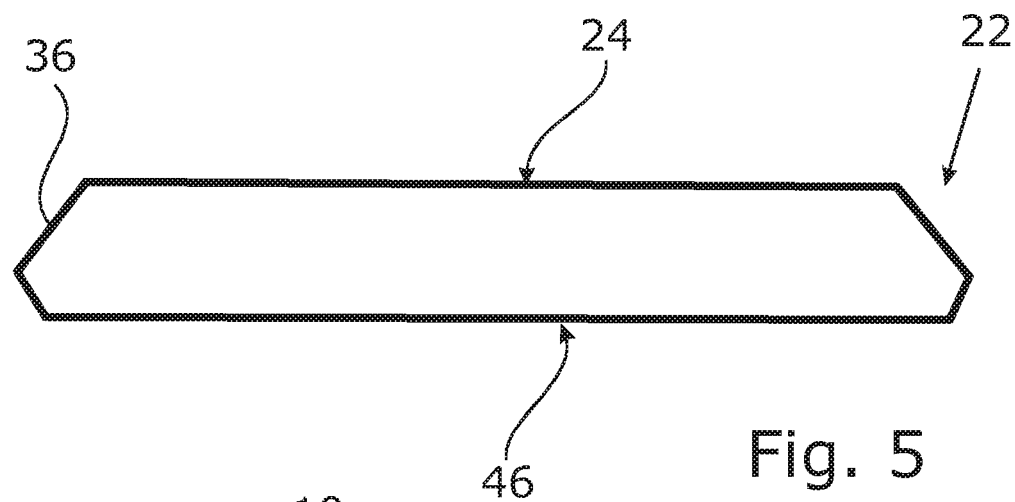

In cross section, the mirror member 22 is configured to be approximately trapezoidal at least in some portions (see FIG. 5), so that its diameter increases at least in some portions, starting from the mirror member surface 24 in the direction towards an underside of the base body 42. The mirror member 22 has a mirror back 46 facing away from the visible mirror surface 24. FIG. 5 shows an embodiment in which the mirror member 22 has a machine diameter in the vertical direction, about in the lower third. This shape simplifies the insertion or snap-in attachment in the mirror-accommodating portion 48. A lower retaining shoulder abuts against the lower region of the outer wall 36.

Figure 4:
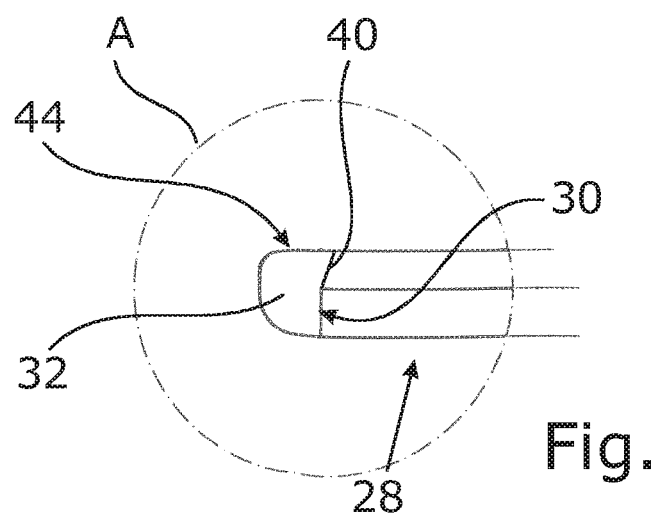
FIG. 4: shows an enlargement of the region A from FIG. 3, FIG. 5: shows a mirror in a side view.

In an enlarged illustration of the region A from FIG. 4, FIG. 4 illustrates that an upper retaining shoulder 40 surrounds the entire outer wall 36 of the mirror member 22 and seals a space next to and below the mirror member 22. The seal is improved by means of a bias of the upper retaining shoulder 40. This means that the mirror member 22, when it is inserted into the first base body part 32, is pressed against the upper retaining shoulder 40 and the latter is minimally compressed or elastically deformed.

Furthermore, this variant of an embodiment is advantageous in that the mirror member 22 is embedded almost flush into a bottom surface 44.

FIG. 6 shows the front area of the mirror suction device 10 with a view of the underside 42 of the base body. The second base body part 34 (hatched), which seals the opening 28, is visible.

The invention is not limited to the exemplary embodiments described, but also includes all embodiments acting in an equivalent way. The above-described variant of an embodiment is to be understood only as an example, and not as limiting. It is also possible to combine the technical features shown in any technically meaningful manner.

The invention claimed is:

1. A dental mirror suction device (10) for suctioning liquids and particles from an oral cavity of a patient, with a tubular hollow base body (12) having an inner surface (14), an outer surface (16), a longitudinal axis (X-X), a connection opening (18) for a hose, and a suction opening (20), wherein the inner surface (14) has a mirror member (22) with a mirror-coated surface (24) which is viewable through the suction opening (20) and which is arranged such that the oral cavity is viewable at least in some portions, wherein the tubular hollow base body (12) has a mirror-accommodating portion 48 with a mirror opening (28);

the mirror suction device (10) is configured as a disposable mirror suction device;

the base body (12) consists of only a single part formed integrally and made of a single material; and wherein the mirror-coated surface (24) is comprised of a portion of the inner surface (14) that is substantially planar and is coated with a reflective material, wherein the reflective material is a vapor-coat with chromium, or a reflective paint;

wherein the mirror opening is made of an elastic material and the mirror member (22) has a larger diameter than the mirror opening (28) such that the mirror member (22) is frictionally held in the tubular hollow base body (12).

2. The method in accordance with claim 1, wherein an inner wall (30) of the mirror opening (28) forms an upper support shoulder (40) which makes contact with an outer wall (36) of the mirror member (22).

3. The method in accordance with claim 2, wherein the upper support shoulder (40) is formed by a first base body part (32) and surrounds an entire outer circumference of the mirror member (22).

4. The method in accordance with claim 2, wherein the upper support shoulder (40) prevents the mirror member, from projecting upwards beyond a floor surface within the base body in the suction opening and from being released out of the base body.

* * * * *